(12) United States Patent
Rajendran et al.

(10) Patent No.: US 6,706,481 B2
(45) Date of Patent: Mar. 16, 2004

(54) IN VITRO SELECTION OF SIGNALING APTAMERS

(75) Inventors: Manjula Rajendran, Austin, TX (US); Andrew D. Ellington, Austin, TX (US); Sulay D. Jhaveri, Alexandria, VA (US)

(73) Assignee: Research Development Foundation, Carson City, NV (US)

( * ) Notice: Subject to any disclaimer, the term of this patent is extended or adjusted under 35 U.S.C. 154(b) by 30 days.

(21) Appl. No.: 10/014,973

(22) Filed: Oct. 26, 2001

(65) Prior Publication Data

US 2002/0127581 A1 Sep. 12, 2002

Related U.S. Application Data

(60) Provisional application No. 60/244,010, filed on Oct. 27, 2000.

(51) Int. Cl.[7] .......................... C12Q 1/68; C12P 19/34; C12M 1/34; C07H 21/04
(52) U.S. Cl. ...................... 435/6; 435/91.2; 435/91.51; 435/287.1; 435/287.2; 536/23.1; 536/25.32
(58) Field of Search ....................... 435/6, 91.2, 91.51, 435/287.1, 287.2; 536/23.1, 25.32

(56) References Cited

U.S. PATENT DOCUMENTS

| | | | | |
|---|---|---|---|---|
| 5,688,670 A | * | 11/1997 | Szostak et al. | 435/91.21 |
| 6,399,302 B1 | | 6/2002 | Lannigan et al. | 435/6 |
| 6,426,409 B1 | * | 7/2002 | Winnacker et al. | 536/23.1 |

OTHER PUBLICATIONS

Huizenga, et al. *A DNA Aptamer That Binds Adenosine and ATP.* Biochemistry, vol. 34, 1995, pp. 656–665.

Burke, et al. *RNA Aptamers to the Adenosine Moiety of S–Adenosyl Methionine: Structural Inferences from Variations on a Theme and the Reproducibility of Selex.* Nucleic Acids Research, vol. 25, 1997, pp. 2020–2024.

Famulok, et al. *Aptamers as Tools in Molecular Biology and Immunology.* Curr. Top Microbiol. Immunol, vol. 243, 1999, pp. 123–136.

Jhaveri, et al. *Designed Signaling Aptamers that Transduce Molecular Recognition to Changes in Fluorescence Intensity.* American Chemical Society, vol. 122, 2000, pp. 2469–2473.

Potyrailo, et al. *Adapting Selected Nucleic Acid Ligands (Aptamers_to Biosensors.* Anal. Chem., vol. 70, 1998, pp. 3419–3425.

Patel, et al. *Structure, Recognition and Adaptive Binding in RNA Aptamer Complexes.* J. Mol. Biol., vol. 272, 1997, pp. 645–664.

* cited by examiner

*Primary Examiner*—Jeffrey Siew
*Assistant Examiner*—Joyce Tung
(74) *Attorney, Agent, or Firm*—Benjamin Aaron Adler

(57) ABSTRACT

The present invention provides a method for the in vitro selection of signaling aptamers comprising the steps of synthesizing a DNA pool, the DNA having a random insert of nucleotides of a specific skewed mole ratio; amplifying the DNA pool; transcribing an RNA pool from the amplified DNA using a fluorescently labeled nucleotide; applying the fluorescently labeled RNA pool to an affinity column to remove the high-affinity fluorescent RNA molecules from the fluorescently labeled RNA pool; obtaining a cDNA pool from the high-affinity fluorescent RNA molecules; repeating the amplification and selection steps on the fluorescent RNA molecules and cloning the fluorescent RNA molecules to yield signaling aptamers. Signaling aptamers comprising DNA molecules are also selected for. Also provided is a signaling aptamer that transduces the conformational change upon binding a ligand to a change in fluorescence intensity of the signaling aptamer.

20 Claims, 9 Drawing Sheets

RNA pool    GGGAAGGCACGAC--- N51 ---AGACCCAACCAGCCAGAGACC    SEQ ID NO: 2

Fig. 1A

ATP-40-1    GGGUUGGGAAGAAACUGUGGCACUUCGGUGCCAGCAACCC    SEQ ID NO: 3

Fig. 1B

| | | | |
|---|---|---|---|
| Family 1 | raf15 | (7) | GAAGCAAGCAGGCAACGAACACAGAGAACCGGGGAACUACCGCGCGUGCU | SEQ ID NO: 4 |
| | raf17 | | GAAGCAAGCAGGCAACGAACACAGAGAACCGGGGAACUACCGCGCGUGCC | SEQ ID NO: 5 |
| | raf134 | | GAAGCAAGCAGGCAACGAACACAGAGAACCGGGGAACUACCGCGCGUGCG | SEQ ID NO: 6 |
| Family 2 | raf10 | (5) | CGCGGGGUAAACAGGGGCAAAAAGCGGCAGGGCCCAGAAGGAUAACAGUAGCA | SEQ ID NO: 7 |
| Family 3 | raf111 | | AGGGGACGGAGCCC-UAAGACAAAGGAGGGCGGCAGGAUGCCA-AACAGGUAG | SEQ ID NO: 8 |
| | raf18 | | AGGGGACGGAGCCCCCAAAGACAAAGGAGGGCGGCAGGAUGCCAGAACAGGUAG | SEQ ID NO: 9 |
| | raf133 | | AGGGGACGGAGCCC-AAAGACAAAGGAGGGCGGCAGGAAGCCA-AACAGGUAG | SEQ ID NO: 10 |
| Family 4 | raf17 | (3) | GAAGAGAGCCGGCGGCGCGAGGCAGGAGAAGAACCGGCCGCACGGAGGG | SEQ ID NO: 11 |
| Family 5 | raf14 | | GCACCGACGAGGAGGAGGAGGGGGAGGGCGCCGUAGCCGGGCGGGG | SEQ ID NO: 12 |
| | raf120 | | GCACCGACGAGGAGGAGGUGGAGGGGAGGAGAAGGCGCCGUAGCCGGAAGGG | SEQ ID NO: 13 |
| | raf126 | | GAGGCCAGGAGACGAACCAACAAGGCAGGCAGAGCCCGGUGCAC | SEQ ID NO: 14 |
| | raf128 | | CGCGCAAGAUACCGCCCGACAGCGGAAGGAGGGCAUGCCGGUCCAGGGCUG | SEQ ID NO: 15 |

Fig. 1C

IN VITRO SELECTION OF SIGNALING APTAMERS

CROSS-REFERENCE TO RELATED APPLICATIONS

This non-provisional application claims benefit of provisional application U.S. Ser. No. 60/244,010, filed Oct. 27, 2000, now abandoned.

BACKGROUND OF THE INVENTION

1. Field of the Invention

The present invention relates generally to the fields of biochemistry and nucleic acid chemistry. More specifically, the present invention relates to in vitro selection of RNA nucleic acid binding species containing from one to three identical fluorescently labeled nucleotides.

2. Description of the Related Art

Nucleic acid binding species (aptamers) that bind a wide range of targets are readily selected from random sequence populations.[3-6] Selected aptamers can recognize molecules as simple as amino acids[7] or as complex as red blood cell membranes[8]. The incorporation of chemically modified bases into aptamers drastically improves their stabilities and potentially renders them suitable for use in homogenous assays with sera or urine samples.

Reagentless biosensors that can directly transduce molecular recognition to optical signals can potentiate the development of sensor arrays for a wide variety of analytes. Pluripotent nucleic acid binding species, aptamers, are readily selected, but can be difficult to adapt to biosensor applications. The adaptation of selected nucleic acid binding species (aptamers) to function as biosensors can further potentiate numerous diagnostic applications.[1,2]

Some nascent examples of aptamer biosensors have already been developed. Fluorescently labeled aptamers and capillary electrophoresis coupled to laser induced fluorescence (CE-LIF) have been used to sensitively detect IgE and thrombin in solution. A labeled anti-thrombin aptamer immobilized on a glass support can detect thrombin in solution by following changes in evanescent-wave-induced fluorescence anisotropy[10]. Labeled anti-CD4 aptamers are used to stain mouse T cells that express human CD4[11]. A labeled anti-human neutrophil elastase (HNE) aptamer is as effective as an anti-anti-human neutrophil elastase antibody for detecting human neutrophil elastase on beads[12].

However, these analytical methods are essentially mimics of methods already developed with antibodies, and generally rely upon an indirect readout of binding following washing or other separation techniques. In contrast, molecules that can directly signal the presence of analytes are proving increasingly useful as biosensors[13]. For example, a mutant of the E. coli phosphate binding protein labeled with a fluorescent dye at the edge of its binding site[14] exhibited a large increase in fluorescence upon inorganic phosphate-binding.[15] A similarly labeled maltose binding protein quantitatively detects maltose in solution[16], while a labeled glucose binding protein detects glucose[17]. The conjugation of both acceptor and donor fluorophores to cAMP-dependent protein kinase yielded a sensor in which fluorescence resonance energy transfer (FRET) is modulated by cAMP[18].

Aptamers that bind small molecules have been shown to undergo conformational changes upon interactions with their cognate ligands[19,20]. A reporter fluorophore introduced into an aptamer in a region known to undergo conformational change can lead to a change in fluorescence intensity after the binding event. However, such an introduction of a fluorophore may result in a significant loss of binding energy, possibly due to steric hindrance or the perturbation of the conformational equilibrium.

Given that functional nucleic acids contain only four monomers with limited chemistries, and that nucleic acid structure is largely predicated on Watson-Crick pairs in which nucleotides are co-dependent, it is surprising that binding species and catalysts can b e selected from random sequence pools that are substantially depleted in a given nucleotide. However, Rogers and Joyce[22] have shown that ribozymes lacking cytidine can be selected following continuous evolution of the Bartel Class I ligase. While aptamers and ribozymes can be selected from pools depleted in one of the nucleotides, a functional price is apparently paid for the lost chemistry and structure. The C-less ribozyme is roughly 100 to 10,000-fold slower than comparable ribozymes that contain cytidine.

It is advantageous, therefore, to reduce the apparent dissonance between ligand-binding and fluorescent signaling. A b initio selection methods that yield signaling aptamers containing only a few identical residues of a fluorescent nucleotide provide such a means. These selected signaling aptamers couple the broad molecular recognition properties of their aptamers with signal transduction.

The prior art is deficient in the lack of in vitro selection methods for signaling aptamers. The present invention fulfills this long-standing need and desire in the art.

SUMMARY OF THE INVENTION

The present invention provides a method of selecting signaling aptamers in vitro comprising the steps: synthesizing a DNA pool so that the DNA has a random insert of nucleotides in a specific skewed mole ratio; amplifying the DNA pool; transcribing an RNA pool from the amplified DNA wherein a nucleotide used in the RNA transcription is fluorescently labeled; applying the fluorescently labeled RNA pool to an affinity column wherein high-affinity fluorescent RNA molecules are removed from the fluorescently labeled RNA pool; obtaining a cDNA pool from the high-affinity fluorescent RNA molecules; repeating the amplification and selection steps on the fluorescent RNA molecules and cloning the fluorescent RNA molecules where the clones comprise signaling aptamers.

The present invention also provides a method of selecting signaling aptamers in vitro comprising the steps of synthesizing a DNA pool, where said DNA has a random insert of nucleotides and said nucleotides comprise a skewed mole ratio; amplifying the DNA pool wherein a nucleotide used in the DNA amplification is labeled with one or more reporter molecules; isolating the labeled single-stranded DNA from the amplified DNA; applying the labeled single-stranded DNA pool to an affinity column wherein high-affinity labeled DNA molecules are removed from the labeled DNA pool; repeating steps (a) through (d) so as to retain the high-affinity labeled DNA pool on the affinity column; and cloning the retained labeled DNA molecules where the clones comprise signaling aptamers.

In another embodiment of the present invention, there is provided a signaling aptamer that transduces the conformational change upon binding a ligand to a change in fluorescence intensity of a fluorescently labeled nucleotide incorporated into the RNA sequence of the signaling aptamer. Additionally, the fluorescently labeled nucleotide may be incorporated into a DNA signaling aptamer.

In a preferred embodiment of the present invention there is provided a fluoresceinated RNA anti-adenosine signaling aptamer.

BRIEF DESCRIPTION OF THE DRAWINGS

So that the matter in which the above-recited features, advantages and objects of the invention, as well as others which will become clear, and are attained and can be understood in detail, more particular descriptions of the invention are briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the sequence of the RNA pool used for selection. The 51-nucleotide random sequence region of this pool is skewed (33.1% A, C, and G, 6% U). Uridine residues are completely replaced by F-12-U.

FIG. 1B shows the minimal anti-adenosine aptamer selected by Sassanfar and Szostak[23].

FIG. 1C shows the sequences of the 51 nucleotide random region from cloned aptamers. The numbers of identical clones are in parentheses. Underlined residues indicate a six-nucleotide motif shared by sequences in Family 1 and Family 2.

FIG. 4 shows the response curves for signaling aptamers in the presence of other nucleotides (FIG. 4A) and in the presence of 1% serum (FIG. 4B).

DETAILED DESCRIPTION OF THE INVENTION

Figure 1D:
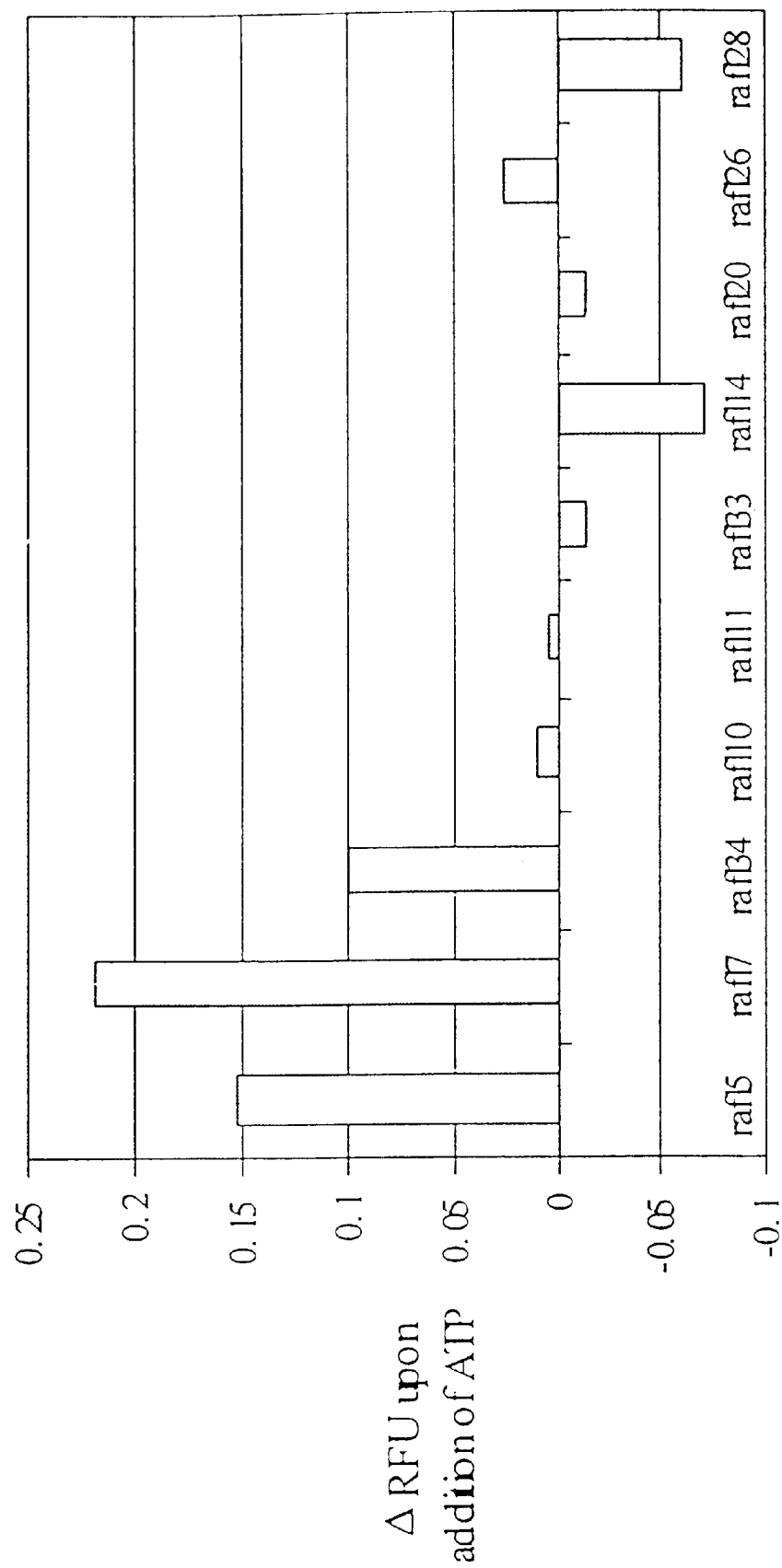
FIG. 1D shows the screen for signaling aptamers. The signaling abilities of aptamers (100 nM) in the presence of 200 mM ATP are shown.

One embodiment of the present invention is a method of selecting signaling aptamers in vitro comprising the steps: synthesizing a DNA pool where the DNA has a random insert of nucleotides where the nucleotides comprise a specific skewed mole ratio; amplifying the DNA pool; transcribing an RNA pool from the amplified DNA so that a nucleotide used in the RNA transcription is fluorescently labeled; applying the fluorescently labeled RNA pool to an affinity column such that high-affinity fluorescent RNA molecules are removed from the fluorescently labeled RNA pool; obtaining a cDNA pool from the high affinity fluorescent RNA molecules; repeating the amplification and selection steps on the high affinity fluorescent RNA molecules and cloning the selected fluorescent RNA molecules where the clones comprise signaling aptamers.

In an aspect of this embodiment the nucleotides used in the RNA amplification may be chemically-modified. Preferably, the DNA has a random insert of 51 nucleotides skewed in the mole ratio of 3:3:2:0.38 A:C:G:T. The fluorescent label may be a fluorescent dye and is appended to a specific nucleotide wherein said fluorescently labeled nucleotide is incorporated into the RNA during transcription. Representative examples of a fluorescent dye are fluorescein, Cascade Blue and Rhodamine Green. Preferably, the fluorescent RNA contains from about one to three nucleotides bearing the fluorescent label wherein the fluorescent RNA is a signaling aptamer. In a preferred embodiment of the present invention, there is provided a selected signaling aptamer containing from one to three fluoresceinated uridines.

Another embodiment of the present invention is a method for the in vitro selection of a DNA signaling aptamer comprising the steps of synthesizing a DNA pool, where said DNA has a random insert of nucleotides and said nucleotides comprise a skewed mole ratio; amplifying the DNA pool where a nucleotide used in the DNA amplification is labeled with one or more reporter molecules; isolating the labeled single-stranded DNA from the amplified DNA; applying the labeled single-stranded DNA pool to an affinity column wherein high-affinity labeled DNA molecules are removed from the labeled DNA pool; repeating steps (a) through (d) so as to retain the high-affinity labeled DNA pool on the affinity column; and cloning the retained labeled DNA molecules wherein the clones comprise signaling aptamers.

In an aspect of this embodiment the nucleotides used in the DNA amplification may be chemically-modified. Preferably, the DNA has a random insert of 51 nucleotides skewed in the mole ratio of 3:3:2:0.38 A:C:G:T. The fluorescent label may be a fluorescent dye and is appended to a specific nucleotide or to a primer wherein said fluorescently labeled nucleotide is incorporated into the DNA during amplification. Representative examples of a fluorescent dye are fluorescein, Cascade Blue and Rhodamine Green. Preferably, the fluorescent DNA contains from about one to three nucleotides bearing the fluorescent label wherein the fluorescent DNA is a signaling aptamer.

Yet another embodiment of the present invention is a selected signaling aptamer comprising an RNA or a DNA nucleic acid binding species (aptamer) wherein the aptamer contains from about one to three fluorescently labeled identical nucleotides. The selected signaling aptamer transduces the conformational change upon binding a ligand to a change in fluoresecence intensity of the fluorescent dye incorporated into the signaling aptamer. In a preferred embodiment of the present invention, the signaling aptamer is a fluoresceinated anti-adenosine RNA aptamer.

As used herein, the term "aptamer" or "selected nucleic acid binding species" shall include non-modified or chemically modified RNA or DNA. The method of selection may be by, but is not limited to, affinity chromatography and the method of amplification by reverse transcription (RT) or polymerase chain reaction (PCR).

As used herein, the term "signaling aptamer" shall include aptamers with reporter molecules, preferably a fluorescent dye, appended to a nucleotide in such a way that upon conformational changes resulting from the aptamer's interaction with a ligand, the reporter molecules yields a differential signal, preferably a change in fluorescence intensity.

As used herein, the term "ligand" shall include any molecule that binds to the signaling aptamer.

As used herein, the term "appended" shall include, but is not limited to, the incorporation of a fluorescently labeled nucleotide during the transcription of the RNA comprising the signaling aptamer.

As used herein, the term "PCR" refers to the polymerase chain reaction that is the subject of U.S. Pat. Nos. 4,683,195 and 4,683,202 to Mullis, as well as other improvements now known in the art.

As used herein, the term "bases" refers to both the deoxyribonucleic and ribonucleic acids. The following abbreviations are used, "A" refers to adenine as well as to it deoxyribose derivative, "T" refers to thymine "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods of the present invention.

Table 1 provides detailed information on the selected signaling aptamers of the present invention.

TABLE 1

| Signaling Aptamer | Aptamer Type | Fluorescent Dye | No. of Uridines | Signals |
|---|---|---|---|---|
| raf15 | RNA anti-ATP | fluorescein | 3 | Yes |
| raf17 | RNA anti-ATP | fluorescein | 2 | Yes |
| raf17-U61C | RNA anti-ATP | fluorescein | 1 | Yes |
| raf17-U52C | RNA anti-ATP | fluorescein | 1 | No |
| raf17s | RNA anti-ATP | fluorescein | 1 | Yes |
| raf134 | RNA anti-ATP | fluorescein | 2 | Yes |
| raf110 | RNA anti-ATP | fluorescein | 3 | slight |
| raf111 | RNA anti-ATP | fluorescein | 3 | slight |
| raf18 | RNA anti-ATP | fluorescein | 2 | n.d. |
| raf133 | RNA anti-ATP | fluorescein | 1 | negative |
| raf114 | RNA anti-ATP | fluorescein | 1 | negative |
| raf120 | RNA anti-ATP | fluorescein | 2 | negative |
| raf126 | RNA anti-ATP | fluorescein | 1 | slight |
| raf128 | RNA anti-ATP | fluorescein | 4 | negative |
| raRG7b | RNA anti-ATP | Rhodamine Gr. | 1 | Yes |
| raCB7b | RNA anti-ATP | Cascade Blue | 1 | Yes |
| raTR7b | RNA anti-ATP | Texas Red | 1 | No |

The present invention is directed toward a method of selecting signaling aptamers in vitro wherein the signaling aptamers contain from about one to three fluorescently labeled identical nucleotides. Additionally, the present invention is directed toward such a signaling aptamer wherein the signaling aptamer transduces a conformational change upon binding a ligand to a change in the fluorescence intensity of the fluorescent nucleotide incorporated therein.

Aptamers undergo ligand-induced conformational changes. In order to convert aptamers to signaling aptamers, reporter molecules are introduced into the aptamers. The reporter molecules perceive a change in their local chemical environment as a result of the conformational change, and as result may signal the conformational change and hence the ligand-binding event.

In order to generate signaling aptamers, a fluorescent or other reporter(s) is introduced into the naïve random sequence pool. For example, nucleotides bearing fluorescent reporters can b e introduced into the pool using DNA or RNA polymerases. Similarly, primers bearing fluorescent reporters or nucleotides that contain reporter(s) can be introduced into DNA pools. Aptamers are selected from such pools based on their ability to bind to a target molecule. The selected aptamers will of necessity accommodate the presence of the fluorescent reporters. Since aptamers undergo ligand-induced conformational changes, the extant fluorescent reporters may also undergo a change in their local chemical environment and signal the conformational change accordingly.

The post-selection introduction of a fluorescent or other reporter into the aptamer may disrupt the binding or other functional capabilities of an aptamer. However, the pre-selection introduction of a fluorescent reporter allows the selection of aptamers in which the fluorescent reporter can not post facto disrupt the binding or other functional capabilities of aptamers as those aptamers whose binding or other functional capabilities are disrupted will be lost during the course of the in vitro selection; only aptamers that can functionally accommodate the fluorescent reporter remain in the population.

The following examples are given for the purpose of illustrating various embodiments of the invention and are not meant to limit the present invention in any fashion.

EXAMPLE 1

Materials

Agarose affinity resins and the derivatives of ATP used to test the specificity of signaling aptamers were purchased from Sigma (St. Louis, Mo.). Fluorescein-12-UTP was purchased from Roche Diagnostics (Indianapolis, Ind.) The other fluorescent UTP conjugates, Cascade Blue-7-UTP, Texas Red-5-UTP, and Rhodamine Green-5-UTP, were purchased from Molecular Probes (Eugene, Oreg.).

EXAMPLE 2

Fluorescence Measurements

All fluorescence measurements were taken on a Series 2 Luminescence Spectrometer from SLM-AMINCO (Spectronic Instruments, Rochester, N.Y.). The experimental samples were excited at the excitation maxima for the corresponding dyes ($\lambda_{ex}$ 494 nm for fluorescein, 505 nm for rhodamine green, 400 nm for cascade blue), and fluorescence intensity was measured at the corresponding emission maximum ($\lambda_{ex}$ 521 nm for fluorescein, 533 for rhodamine green, and 420 for cascade blue). The 1 ml aptamer solutions were pipetted into a fluorimeter cell (Starna Cells, Inc., Atascadero, Calif.) and ligand solutions of varying concentrations were added in small volumes.

EXAMPLE 3

Fluorescence Response Curves

Fluorescent aptamers (50 nM) were thermally equilibrated in binding buffer. On average, eight readings were taken to establish the initial fluorescence intensity of the aptamer. ATP solutions of varying concentrations in binding buffer were added in increments of 2 μl. The change in fluorescence upon addition of ATP was plotted; in order to standardize the presentation of data, the fluorescence change at a given ATP concentration ($F_x-F_0$) was divided by the fluorescence change at saturating ATP concentrations ($F_{100}-F_0$). The data were fitted to the following equation using the program Kaleidograph (Synergy, Reading, Pa.): Y=AX/(X+

B); where Y=the relative increase in fluorescence at a given ATP concentration, $(F_x-F_0)/(F_{100}-F_0)$; X=concentration of ATP; A=the increase in fluorescence at saturating ATP concentrations, $(F_{100}-F_0)$; and B=the apparent dissociation constant value (concentration of ATP at Y=0.5 A).

EXAMPLE 4
Preparation of a Fluorescent RNA Pool

In order to generate signaling aptamers that yield large signals and low background, only a few fluorescent residues should be present in each binding species. If multiple fluorescent residues are present, many of them are not affected by localized conformational changes and therefore present an intrinsic fluorescent background that makes the identification of signaling aptamers more difficult thereby decreasing the overall magnitude of signaling.

Therefore, a pool of RNA molecules (N51) is generated (FIG. 1A) in which a 51 residue random sequence region is skewed so that U residues are poorly represented (33.1% A, C, and G, 6% U). The resulting population of RNAs is described by a binomial distribution wherein a major fraction of the population contained only three to four uridine per molecule $(Y=[51!/((X!)(51-X)!)] (0.06)^X (0.94)^{(51-x)}$, where Y=fraction of the population, and X=number of uridines per molecule). The recent selection of C-less ribozymes[22] proves that functional nucleic acid molecules potentially can b e selected from pools lacking one of the four bases, and, therefore, that anti-adenosine aptamers can be selected from a U-poor pool.

Specifically, a 102-mer DNA pool (N51; 5'TAATACGACTCACTATAGGGAAGGCACGAC-N$_{51}$-AGACCCAACCAG CCAGAGACC (SEQ ID NO: 1)) (FIG. 1A) with a random insert of 51 nucleotides was synthesized. Each N represents a mixture of A, C, G, and T in a mole ratio of 3:3:2:0.38 A:C:G:T phosphoramidites. The single-stranded DNA pool was deprotected, purified, and PCR-amplified according to a standard protocol[33]. Only 10% of the resultant DNA pool was amplifiable. A fluorescent RNA pool was transcribed from the double-stranded DNA pool using a T7 Ampliscribe in vitro transcription kit (Epicentre, Madison, Wis.) with 1 mM F-12-UTP substituting for UTP. Following DNAse digestion to remove the dsDNA template, fluorescently labeled RNA was purified on a 10% polyacrylamide gel, eluted overnight at 37° C. in a 0.3 M NaCl solution, and ethanol precipitated. The pool was resuspended in 15 µl H$_2$O and subsequently quantitated by measuring the A$_{260}$ using an extinction coefficient of 0.025 ml cm$^{-1}$ µg$^{-1}$. This is a standard extinction coefficient for non-fluorescent nucleic acids[34] and was adopted because fluorescein has an extinction coefficient near 260 (21,000 M$^{-1}$cm$^{-1}$) that is similar to that of a nucleotide. Thus, the addition of a few fluorescein labels should not greatly perturb the overall extinction coefficient of the nucleic acid pool.

EXAMPLE 5
In Vitro Selection of Fluorescently Labeled RNA Aptamers

The selection of fluorescently-labeled, anti-adenosine aptamers is carried out in essentially the same manner as the original selection for anti-adenosine aptamers[23]. The initial RNA pool contained approximately 2x10$^{14}$ sequences. Following thermal denaturation in binding buffer (300 mM NaCl, 20 mM Tris-Cl, pH 7.4, 5 mM MgCl$_2$) for 3 minutes at 65° C. and equilibration to room temperature, the pool was passed through an 0.5 ml agarose column to remove those species that bound to the column matrix. Subsequently, the pool (ranging from 4–30 µg during the course of the selection) was applied to an ATP-agarose affinity column (ATP linked through its C8 via a diaminohexyl linker to cyanogen bromide-activated agarose), and allowed to equilibrate for 10 minutes. The concentration of ATP in the column was 2.3 mM, and the volume of the affinity column ranged from 0.2 ml to 1 ml during the course of the selection. Low-affinity binding species were removed by developing the column with from 15 to 104 column volumes of binding buffer. High-affinity species were eluted from the column in from 0.4 to 3 ml binding buffer containing 5 mM ATP. Following concentration via ethanol precipitation, the resulting enriched pool of fluorescent RNA molecules was reverse transcribed to a cDNA pool, amplified by PCR, and fluorescent RNA for the next round was generated by in vitro transcription. In the last three rounds, the pool was first passed over a 0.5 ml GTP agarose column as a negative selection. After 11 rounds of selection and amplification, a third of the fluorescent RNA pool is retained on an ATP agarose column following 8 column volumes of elution; in initial rounds less than 1% of the pool was specifically retained and eluted. Furthermore, it is possible to generate fluorescent RNA via transcription by using a chemically-modified nucleotide during the transcription process Aptamers from round 11 were cloned using a TOPO TA cloning kit (Invitrogen, Carlsbad, Calif.) and the sequences of 24 aptamers were determined using a SequiTherm EXCEL II kit (Epicentre, Madison, Wis.). On average, 2.25 uridines were present per selected sequence, indicating that little or no selection against the incorporation of the modified base occurred. Aptamers were readily divided into five families based on sequence similarities, with two outliers (FIG. 1C). Families 1 and 2 appear to share a six-residue sequence motif, CAGAAG (SEQ ID NO: 16). FIG. 1B shows the minimal anti-adenosine aptamer selected by Sassanfar and Szostak[23]

Raf17 is the first example of an aptamer selected from a pool significantly depleted in one of the nucleotides. Other aptamers from this pool (Family 4, FIG. 1C) contain no uridine residues. It is especially encouraging that functional nucleic acids could be selected from a pool depleted in U, rather than C, since uridines remaining in the C-less pool can pair with both purines, while cytidines remaining in the U-poor pool should primarily pair with guanosine and not adenosine. These results further demonstrate that the primordial evolution of nucleic acid replicators and catalysts may have not required a full complement of genetic information[24,25].

EXAMPLE 6
Screening Aptamers for Signaling Function

The final pool of fluoresceinated RNA displays a slight signaling capability. When 600 nM of the pool is allowed to equilibrate in the presence of 2 mM ATP, it showed an increase in relative fluorescence of 7%. Representatives of the different families of sequences were assayed for signaling in the presence of 200 µM ATP (FIG. 1D). Only aptamers from Family 1 displayed significant, positive signaling ability (increase in fluorescence), and raf17 was the best signaling aptamer. An aptamer from Family 5 and an outlier, raf128, displayed some negative signaling ability (decrease in fluorescence).

EXAMPLE 7
Mapping Signaling Residues

Aptamers raf17 and raf15 both signal the presence of adenosine, yet the latter contains one more uridine residue then the former. This comparison suggests that the 3'-most uridine residue in raf15 and other Family 1 members contribute to background fluorescence but are unnecessary for signaling. This is supported by the fact that raf17 (22% increase in relative fluorescence) shows slightly more signaling ability than raf15 (15% increase in relative fluorescence).

Figure 2A:
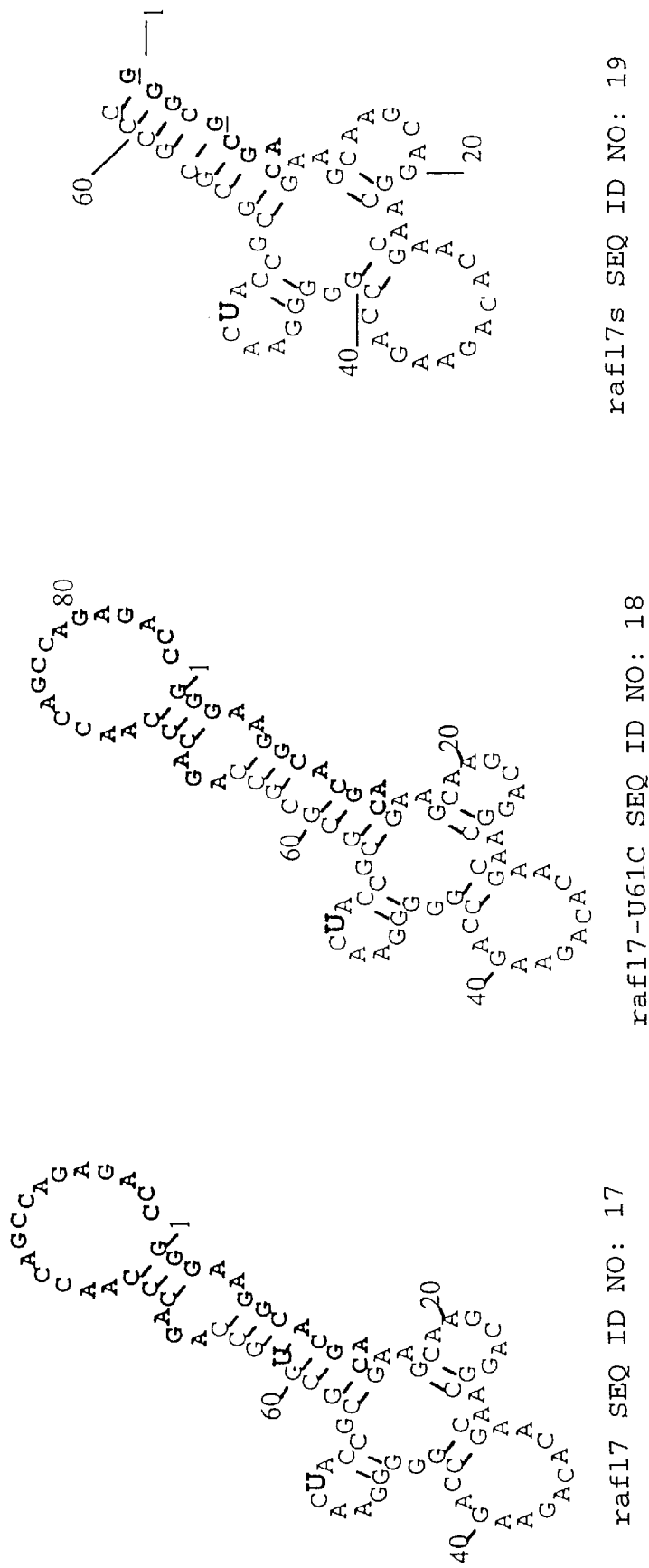
FIG. 2A shows the predicted secondary structures of the signaling aptamers raf17, raf17-U61C, and raf17s. Residues in constant regions are shown in bold. F-12-U residues are highlighted.
Figure 2B:
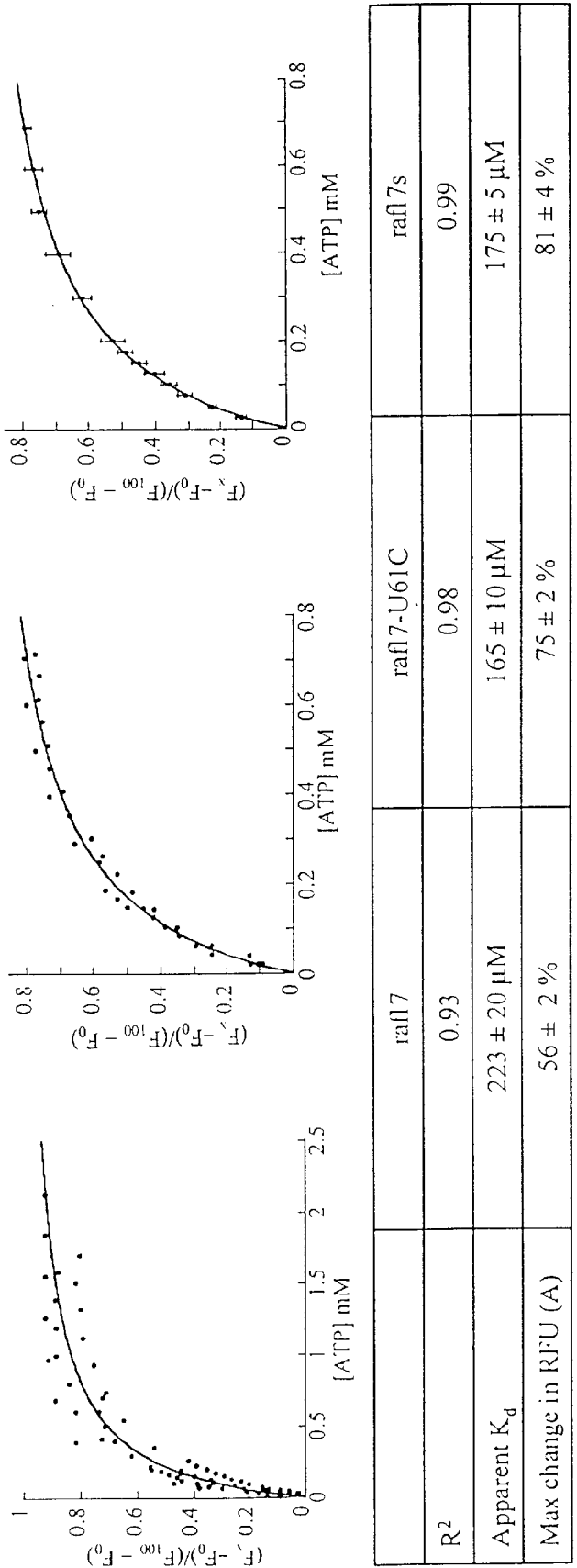
FIG. 2B shows the response curves for signaling aptamers. Multiple data sets were fitted to curves using the equation $Y=AX/(X+K_d)$. The table below the curves shows the calculated curve-fit parameters and the changes in relative fluorescence units (RFU) at saturation.

In order to determine which of the two remaining fluoresceinated uridine residues in raf17 (FIG. 2A) are necessary for signaling, mutants of raf17 were constructed that replace either the uridine at position 52 with cytidine (raf17-U52C), or the uridine at position 61 with cytidine (raf17-U61C). The U52C substitution displays no ATP-dependent changes in fluorescence, while the U61C substitution not only signals, but actually displays a slightly greater ATP-dependent change in fluorescence than the parental molecule, raf17 (FIG. 2B). This is consonant with the hypothesis that as fluorophores unrelated to signaling are removed, signaling improves. Raf17 shows a maximal change in RFU of 56%, with an apparent $K_d$ of 223 µM±20 µM for ATP. Raf17-U61C shows a maximal change in RFU of 75%, with an apparent $K_d$ of 165 µM±10 µM for ATP (FIG. 2B). Overall, the results with different aptamers and mutants demonstrate that the fluoresceinated uridine at position 52 is the only residue required by the Family 1 aptamers for signaling. Moreover, signaling is apparently due to quenching of the fluorescein in the absence of the cognate ligand. When the aptamer is digested with ribonulcease, the maximum fluorescence intensity is equivalent to the fluorescence intensity of the intact aptamer in the presence of saturating concentrations of ATP.

The predicted secondary structure of the aptamer raf17-U61C (FIG. 2A) was examined in order to develop hypotheses regarding what other residues might be important for signaling. The single uridine occurs in an apparent multi-arm junction, away from the constant regions. A truncated version of the aptamer (raf17s) was constructed in which most of the constant regions were removed while the long, predicted stem supporting the multi-arm junction remains. Raf17s supports signaling activity (FIG. 2B). In fact, the signaling activity improves so that the maximal change in RFU was 81% the apparent $K_d$ was 175 µM±5 µM essentially the same as that of the parental aptamer raf17-U61C. Further truncations of raf17s, in which portions of the multi-arm junction were removed did not signal (data not shown).

The U-poor anti-adenosine signaling aptamer had an apparent $K_d$ for ATP that is roughly 200-fold higher than that of the canonical anti-adenosine aptamer ATP-40-1 selected by Sassanfar and Szostak[23], and independently selected by Burke and Gold[26] and Burgstaller and Famulok[27]. However, the selected signaling aptamer does not appear to have a corresponding loss of specificity. These results are consistent with aptamer specificity being due largely to the steric constraints inherent in the structures of the binding pockets, rather than to the formation or loss of hydrogen bonds or salt bridges with individual ligands.

EXAMPLE 8
Specificity of Signaling

Figure 3A:
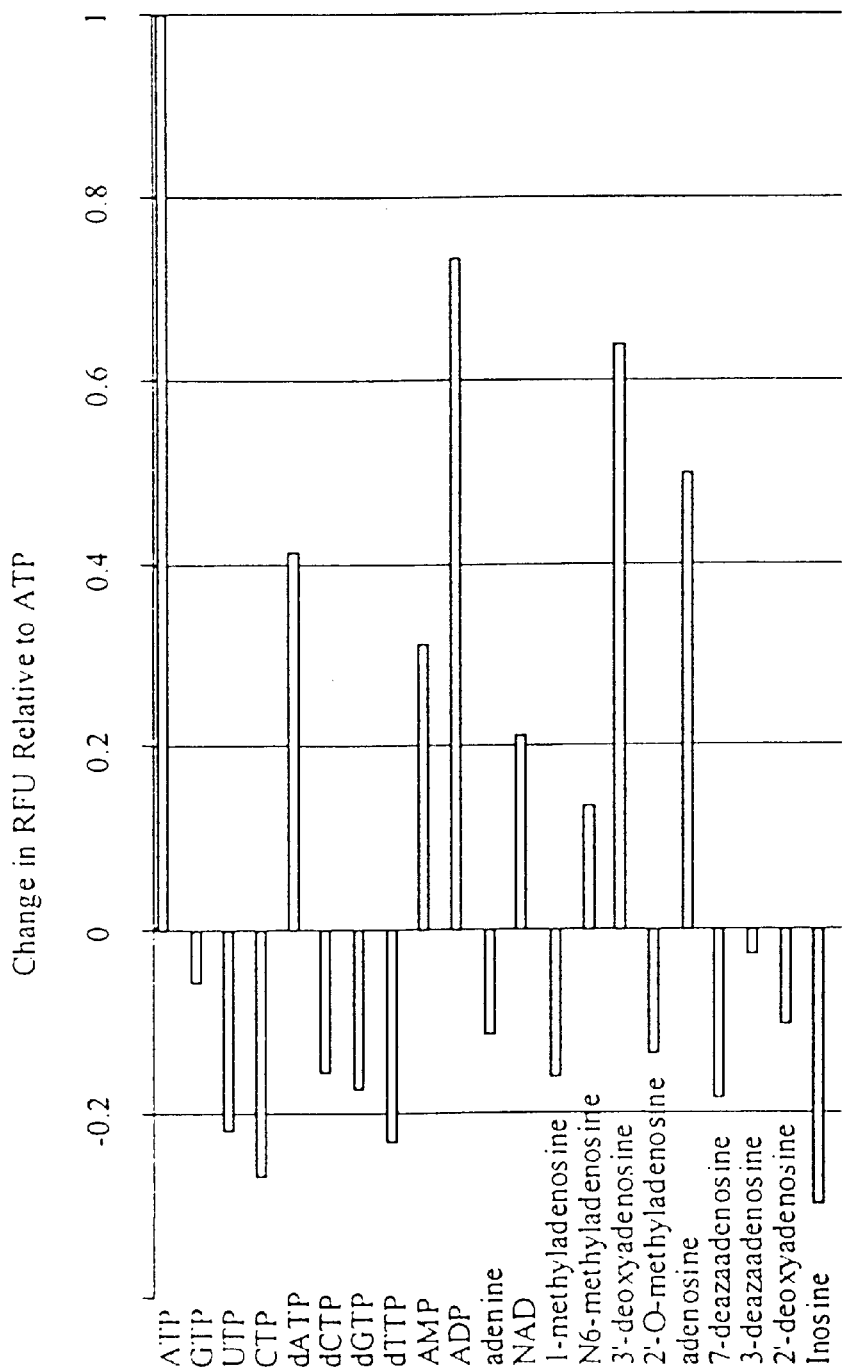
FIG. 3A shows the signaling specificity of raf17-U61C (21 nM). Aptamer raf17-U61C was assayed for signaling in the presence of 200 µM ligand. The change in RFU for different ligands is shown normalized to the change in RFU with ATP.

To assess the specificity of aptamer raf17-U61C, relative changes in fluorescent signal were monitored in the presence of a variety of adenosine derivatives and other nucleotides. These data are shown in FIG. 3A, normalized to the change in fluorescence in the presence of ATP. The aptamer signals in the presence of any adenosine derivative that does not perturb either the nucleobase or the sugar (ATP, ADP, AMP, adenosine, NAD). However, most derivatives in which the nucleobase or sugar differ from adenosine show either no signaling or a slight quenching of the fluorophore. The sole exceptions are N6-methyl adenosine and 2' dATP, which still show some positive signaling ability. Interestingly, 2' deoxyadenosine does not signal. The aptamer may discriminate between 2' dATP and 2' deoxyadenosine because the presence of 5' phosphates seems to generally enhance recognition and signaling; ATP and ADP signal better than AMP and adenosine.

Figure 3B:
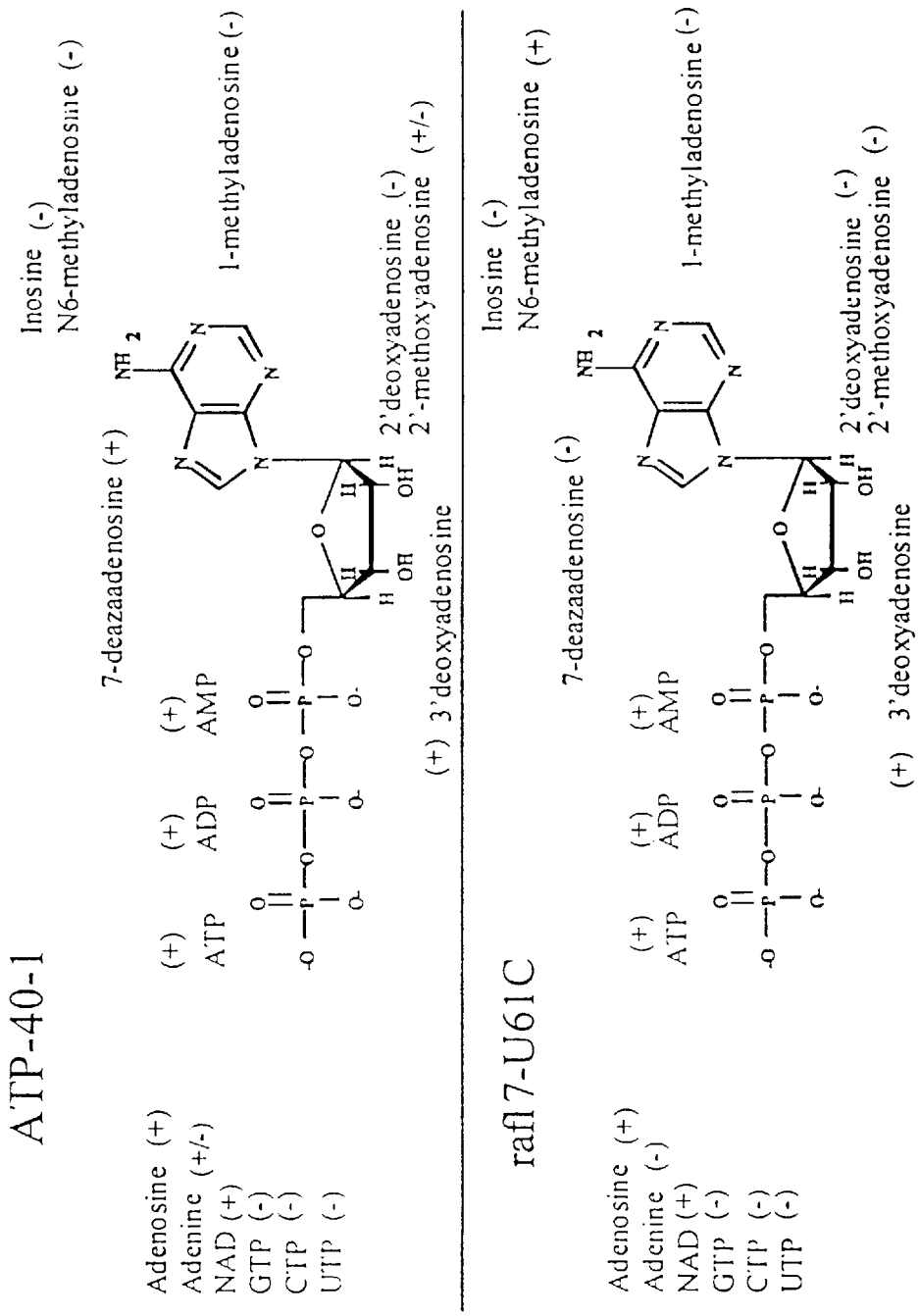
FIG. 3B shows the comparison of the binding specificity reported for ATP-40-1[20] to the positive signaling specificity of raf17-U61C.

Both the signaling aptamer and the anti-adenosine aptamer selected by Sassanfar and Szostak (ATP-40-1)[23] primarily recognize the base and sugar portions of adenosine nucleotides. However, based on the criterion of positive signaling, the specificity of the raf17b signaling aptamer is equal to or better than that of anti-adenosine aptamers selected from pools that contain equal amounts of all four residues (FIG. 3B). The 'U rich' ATP-40-1 also cross-recognizes the adenine, 2'-O-methyladenosine, and 7-deazaadenosine, while the 'U poor' raf17-U61C does not. Conversely, raf17-U61C also recognizes N6-methyl adenosine, while ATP-40-1 does not.

Figures 4A, 4B:
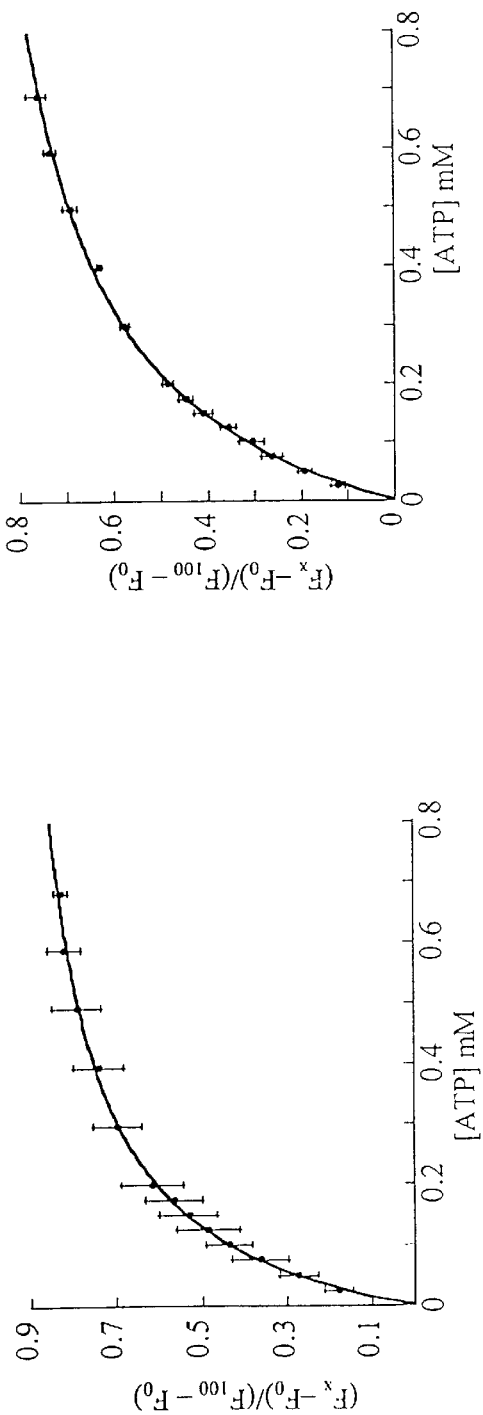
FIG. 4A: An equimolar solution of ATP, GTP, CTP, and UTP was mixed with the signaling aptamer raf17s at varying concentrations.
FIG. 4B: The signaling aptamer raf17s was mixed with varying amounts of ATP. Presentation and values are as in FIG. 2.

It was necessary to determine whether the selected signaling aptamer is specific enough to quantitate ligands in the presence of complex mixtures. Changes in the fluorescence intensity of raf17s were determined as ATP concentrations were varied against a background of GTP, CTP, and UTP (FIG. 4A) or a background of 1% calf serum (FIG. 4B).

In both instances, the signaling aptamer followed the presence and concentration of ATP. However, the apparent $K_d$'s of the signaling aptamer in these two milieu's were quite different: the apparent $K_d$ in the presence of other nucleotides was 127 µM±3 µM, while the apparent $K_d$ in serum was 212 µM±7 µM. Different environments appear to stabilize or destabilize the unliganded, quenched form of the signaling aptamer to different extents. Practically, analyte quantitation in complex mixtures may require the use of standard curve, as is the case for numerous other analytical techniques.

EXAMPLE 9
Selected Signaling Aptamers can Generically Couple Ligand Recognition to Changes in Fluorescence Intensity The mechanism by which raf17-U61C signals is unknown, but it seems likely that U52 undergoes a ligand-dependent change in chemical environment. If so, then there are two possibilities: the ligand-dependent conformational change is dependent on F-12-U, or the ligand-dependent conformational change is independent of F-12-U.

In order to probe these possibilities, the aptamer was transcribed with other UTP analogs: Cascade Blue-7-UTP, Rhodamine Green-5-UTP, and Texas Red-5-UTP. Apart from the obvious differences in optical properties, these analogs also differed in the lengths of the alkyl amino spacer between the fluorophore and the nucleoside (the number of atoms in the spacer is indicated in the name of the analog; Cascade Blue-7-UTP has 7 atoms between the dye and the nucleotide).

Figures 5A, 5B:
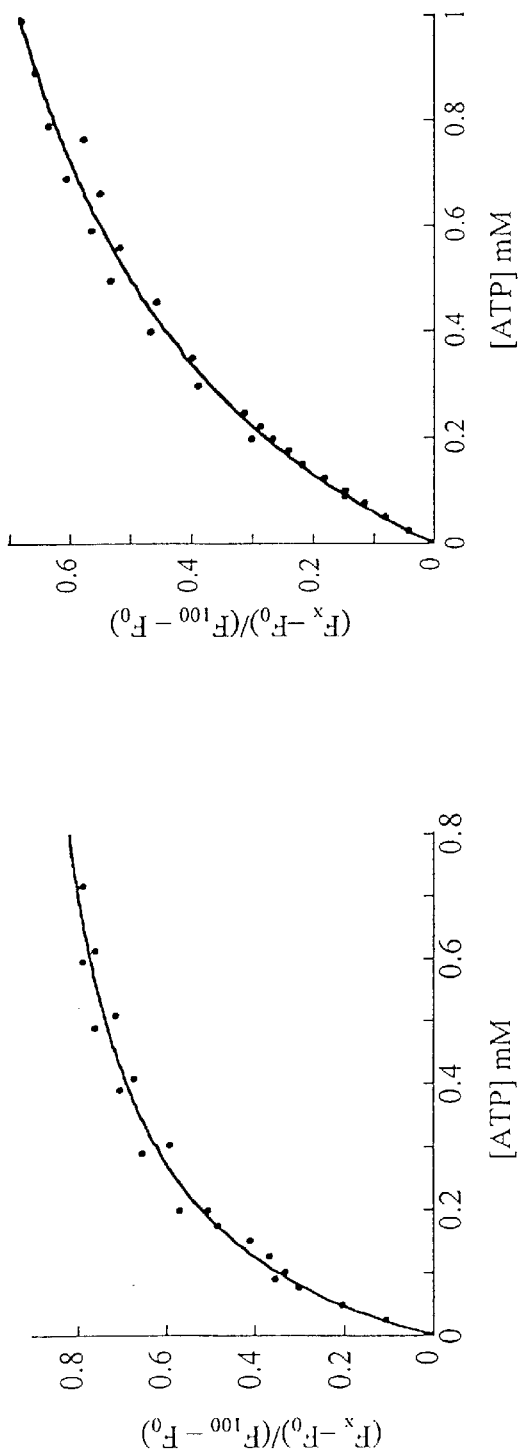
FIG. 5 shows the response curves for signaling aptamers raCB7b (FIG. 5A) and raRG7b (FIG. 5B). Duplicate data sets were fitted to the curves. The table below the curves shows the calculated curve-fit parameters.

Transcription of raf17-U61C with Texas Red (raTR7b) yielded a labeled aptamer that did not signal. Remarkably, though, transcription with Cascade Blue (raCB7b) and Rhodamine Green (raRG7b) in place of F-12-UTP yielded signaling aptamers (FIGS. 5A and 5B). The maximal increase in RFU for raCB7b is 160%, with an apparent $K_d$ of 188±15 µM. The calculated maximal increase in RFU for raRG7b is 220%, with an apparent $K_d$ of 571±39 µM for ATP. Neither aptamer signals in the presence of up to 500 µM GTP.

The few uridines in the selected signaling aptamers are important to function. The fact that quite different uridine-dye conjugates can support signaling by raf17b suggests that binding and conformational changes are strongly coupled to the single remaining uridine residue. This is somewhat surprising, given that fluorescein had as much opportunity as any nucleobase, sugar, or phosphodiester to contribute chemical moieties to ATP-binding during the selection procedure. Modified nucleotides with longer spacer arms (F-12-UTP and Cascade Blue-7-UTP) perturbed binding less than those with shorter spacer arms (Rhodamine Green-5-UTP and Texas Red-5-UTP). This apparent length correlation again indicates the central importance of the uridine residue itself in binding and signaling.

Figure 6:
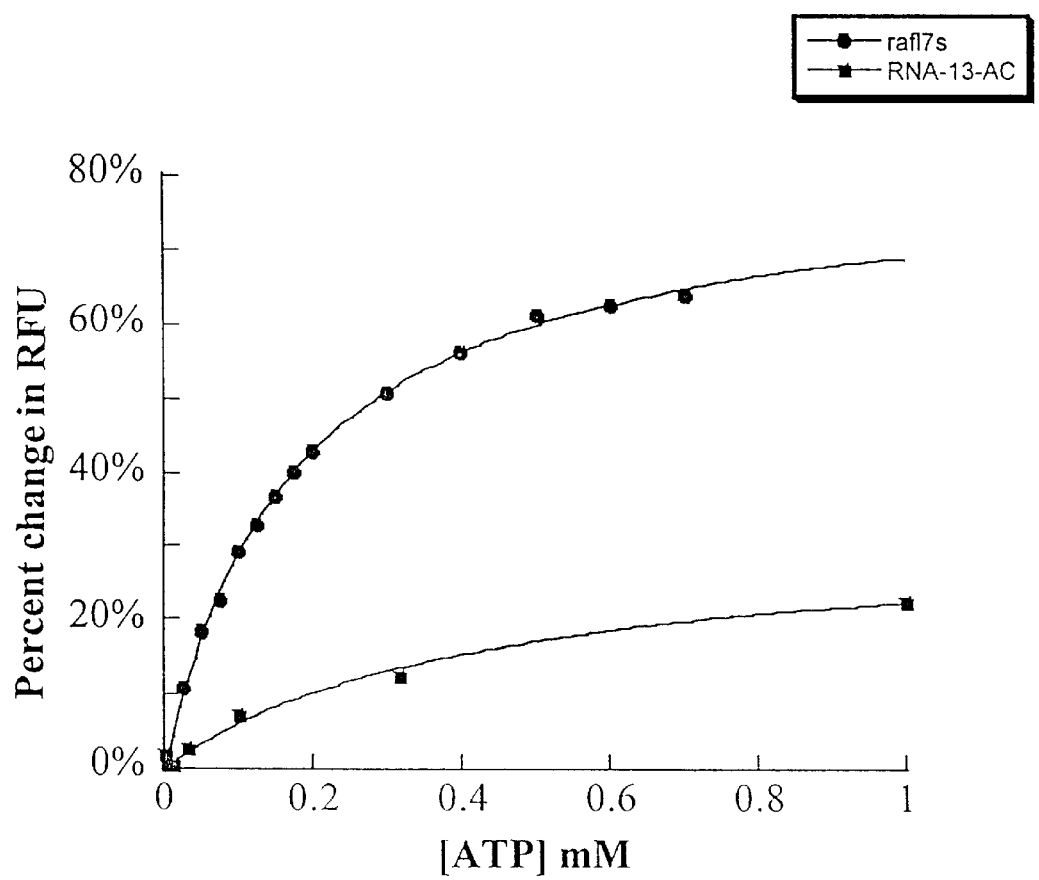
FIG. 6 shows the response curves for the selected signaling aptamer, raf17s, and the designed signaling aptamer, RNA-13-AC[21].

EXAMPLE 10
Sensitivity and Responsivity of Selected and Screened Signaling Aptamers Designed signaling aptamers require an intimate knowledge of three-dimensional molecular structure and must be painstakingly synthesized and assayed prior to use, whereas the selected and screened signaling aptamers require no foreknowledge of structure nor sequence and can be immediately applied as sensor elements. Moreover, selected signaling aptamers have better sensitivities than designed signaling aptamers. The apparent kd of and ATP-40-1 derivative in which residue A13 is replaced with an acridine label is 340±70 $\mu$M, while the basal $K_d$ of raf17s is 175±5 $\mu$M. Selected signaling aptamers also have greatly superior responsivities (FIG. 6). Acridine-conjugated ATP-40-1 has a maximal, adenosine-dependent increase in relative fluorescence of 28±2%[21], whereas the selected and screened signaling aptamers have up to seven-fold greater increases in relative fluorescence. The fact that different fluorophores were utilized in signaling aptamer design (acridine) than in signaling aptamer selection (fluorescein) does not limit the validity of such comparisons, since aptamers in which A13 was replaced with fluorescein showed no signaling capabilities[21].

EXAMPLE 11
In vitro Selection of Fluorescently Labeled DNA Signaling Aptamers It should be clear that corresponding fluorescently labeled DNA signaling aptamers can be readily selected in vitro using the method, with slight modifications to account for a DNA end product, as provided for fluorescently labeled RNA signaling aptamers. These DNA aptamers may incorporate either unmodified or chemically-modified nucleotides. A DNA pool using a random insert of a skewed mole ratio of nucleotides is synthesized and then amplified. Amplification of the DNA may be accomplished via either primers containing one or more reporter molecules or nucleotides containing one or more reporter molecules. Single-stranded DNA is isolated from the amplified DNA and specific binding species of DNA aptamers are selected and subsequently amplified.

EXAMPLE 12
Signaling Aptamers as Diagnostic Reagents

The in vitro selection of aptamers has proven to be an extremely facile and robust method for generating receptors for a variety of targets. Aptamers can now be thought of as universal receptors much the same way that antibodies have previously proved to be. However, unlike antibodies, aptamers are converted into readily synthesized diagnostic reagents that immediately report interactions with cognate ligands in solution[1,2,28].

A fluorescent reporter introduced into an aptamer could yield a change in intensity, anisotropy, lifetime or spectral properties. In particular, the fact that the same signaling aptamer can accommodate multiple different fluorescent dyes bodes well for the application of signaling aptamers in schemes or devices requiring analysis at different wavelengths. Multiple fluors or molecules that modulate the properties of fluors can be introduced into the same aptamer and can undergo coordinated changes in intensity, anisotropy, lifetime, or spectral properties; in addition, changes in fluorescent resonance energy transfer (FRET) is possible.

Based on these features, the further development of high-throughput methods for the selection of signaling aptamers can potentiate the development of sensor arrays that can detect large numbers of non-nucleic acid analytes. Specifically, for example, a useful combination of technologies might involve the chemical synthesis of signaling aptamers on beads and the introduction of these beads directly onto fiber optic cables[29,30] or into etched microwells[31,32].

The following references are cited herein

1. Hesselberth, J., Robertson, M. P., Jhaveri, S. D. & Ellington, A. D. In vitro selection of nucleic acids for diagnostic applications. *Reviews in Molecular Biotechnology* 74, 15–25 (2000).
2. Jayasena, S. D. Aptamers: An emerging class of molecules that rival antibodies in diagnostics. *Clin Chem* 45, 1628–1650 (1999).
3. Famulok, M. & Jenne, A. Oligonucleotide libraries—variatio delectat. *Curr Opin Chem Biol* 2, 320–7 (1998).
4. Gold, L., Polisky, B., Uhlenbeck, O. & Yarus, M. Diversity of oligonucleotide functions. *Annu Rev Biochem* 64, 763–97 (1995).
5. Osborne, S. E., Matsumura, I. & Ellington, A. D. Aptamers as therapeutic and diagnostic reagents: problems and prospects. *Curr Opin Chem Biol* 1, 5–9 (1997).
6. Famulok, M. & Mayer, G. Aptamers as tools in molecular biology and immunology. *Curr Top Microbiol Immunol* 243, 123–36 (1999).
7. Geiger, A., Burgstaller, P., von der Eltz, H., Roeder, A. & Famulok, M. RNA aptamers that bind L-arginine with sub-micromolar dissociation constants and high enantioselectivity. *Nucleic Acids Res* 24, 1029–36 (1996).
8. Morris, K. N., Jensen, K. B., Julin, C. M., Weil, M. & Gold, L. High affinity ligands from in vitro selection: complex targets. *Proc Natl Acad Sci USA* 95, 2902–7 (1998).
9. German, I., Buchanan, D. D. & Kennedy, R. T. Aptamers as ligands in affinity probe capillary electrophoresis. *Anal Chem* 70, 4540–5 (1998).
10. Potyrailo, R. A., Conrad, R. C., Ellington, A. D. & Hieftje, G. M. Adapting selected nucleic acid ligands (aptamers) to biosensors. *Anal Chem* 70, 3419–25 (1998).
11. Davis, K. A., Lin, Y., Abrams, B. & Jayasena, S. D. Staining of cell surface human CD4 with 2'-F-pyrimidine-containing RNA aptamers for flow cytometry. *Nucleic Acids Res* 26, 3915–24 (1998).
12. Davis, K. A., Abrams, B., Lin, Y. & Jayasena, S. D. Use of a high affinity DNA ligand in flow cytometry. *Nucleic Acids Res* 24, 702–6 (996).
13. Giuliano, K. A. & Taylor, D. L. Fluorescent-protein biosensors: new tools for drug discovery. *Trends Biotechnol* 16, 135–40 (1998).
14. Hirshberg, M. et al. Crystal structure of phosphate binding protein labeled with a coumarin fluorophore, a probe for inorganic phosphate. *Biochemistry* 37, 10381–5 (1998).
15. Brune, M. et al. Mechanism of inorganic phosphate interaction with phosphate binding protein from *Escherichia coli*. *Biochemistry* 37, 10370–80 (1998).

16. Gilardi, G., Zhou, L. Q., Hibbert, L. & Cass, A. E. Engineering the maltose binding protein for reagentless fluorescence sensing. *Anal Chem* 66, 3840–7 (1994).
17. Marvin, J. S. et al. The rational design of allosteric interactions in a monomeric protein and its applications to the construction of biosensors. *Proc Natl Acad Sci USA* 94, 4366–71 (1997).
18. Adams, S. R., Harootunian, A. T., Buechler, Y. J., Taylor, S. S. & Tsien, R. Y. Fluorescence ratio imaging of cyclic AMP in single cells. *Nature* 349, 694–7 (1991).
19. Patel, D. J. et al. Structure, recognition and adaptive binding in RNA aptamer complexes. *J Mol Biol* 272, 645–64 (1997).
20. Westhof, E. & Patel, D. J. Nucleic acids. From self-assembly to induced-fit recognition. *Curr Opin Struct Biol* 7, 305–9 (1997).
21. Jhaveri, S. D. et al. Designed Signaling Aptamers that Transduce Molecular Recognition to Changes in Fluorescence Intensity. *Journal of American Chemical Society* 122(11), 2469–2473 (2000).
22. Rogers, J. & Joyce, G. F. A ribozyme that lacks cytidine. *Nature* 402, 323–5 (1999).
23. Sassanfar, M. & Szostak, J. W. An RNA motif that binds ATP. *Nature* 364, 550–3 (1993).
24. Crick, F. H. The origin of the genetic code. *J Mol Biol* 38, 367–79 (1968).
25. Wachtershauser, G. An all-purine precursor of nucleic acids. *Proc Natl Acad Sci USA* 85, 1134–5 (1988).
26. Burke, D. H. & Gold, L. RNA aptamers to the adenosine moiety of S-adenosyl methionine: structural inferences from variations on a theme and the reproducibility of SELEX *Nucleic Acids Res* 25, 2020–4 (1997).
27. Burgstaller, P. & Famulok, M. Isolation of RNA-aptamers for biological cofactors by in vitro selection. *Angew Chem Int Ed Engl.* 33,1084–1087 (1994).
28. Ellington, A. D., Hesselberth, J., Jhaveri, S., Robertson, M. P. Combinatorial methods: aptamers and aptazymes *Proc. SPIE-Int Soc Opt Eng.* 3858, 126–134 (1999).
29. Taylor, L. C., Walt, D. R. Application of high density optical microwell arrays in a live-cell biosensing sstem. *Anal. Biochem* 278(2), 132–142 (2000).
30. Walt, D. R. Techview:Molecular biology: Bead-based fiber-optic arrays *Science* (Washington, D.C.) 287(5452), 451–452 (2000).
31. Savoy, S. et al. Solution based analysis of multiple analytes by a sensor array: toward the development of an "electronic tongue" *Proc SPIE-Int Soc Opt Eng* 3539 (Chemical microsensors and applications), 17–26 (1998).
32. Lavigne, J. J. et al. Single-analyte to multianalyte fluorescence sensors Proc SPIE-Int Soc Opt Eng. 3602 (Advances in Fluorescence Sensing Technology IV), 220–231 (1999).
33. Pollard, J., Bell, S., Ellington, A., *Design, Synthesis, and Amplification of DNA pools for In Vitro Selection*, 9.2.1–23 In Press (John Wiley & Sons, Inc., New York, N.Y., 1999).
34. Gallagher. *Quantitation of DNA and RNA with Absorption and Fluorescence Spectroscopy*, A.3D.1–8 (John Wiley & Sons, Inc., New York, N.Y., 1996).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of selecting signaling aptamers in vitro comprising the steps of:
   (a) synthesizing a DNA pool, said DNA having a random insert of fifty-one nucleotides, wherein a A:C:G:T mole ratio of amounts of each nucleotide in said random insert is skewed such that the amounts of only three of said nucleotides are about equal
   (b) amplifying the DNA pool;
   (c) transcribing an RNA pool from said amplified DNA wherein a nucleotide used in the RNA transcription is labeled with one or more reporter molecules;
   (d) applying the labeled RNA pool to an affinity column wherein labeled RNA molecules having a high binding affinity for the column are retained on the affinity column and thereby removed from the labeled RNA pool;
   (e) obtaining a cDNA pool from the labeled RNA molecules retained on the affinity column;
   (f) repeating steps (a) through (e) to retain the labeled RNAs from the labeled RNA pool having a high binding affinity for the column on the affinity column; and
   (g) cloning the retained labeled RNA molecules, said clones comprising signaling aptamers.

2. The method of claim 1, wherein the nucleotide used in the RNA transcription is a chemically-modified nucleotide.

3. The method of claim 1, wherein the DNA having the random insert of fifty-one nucleotides has the sequence shown in SEQ ID NO: 1.

4. The method of claim 1, wherein the skewed mole ratio of the random insert of said nucleotides is 3:3:2:0.38 A:C:G:T.

5. The method of claim 1, wherein steps (a) through (e) are repeated until about one third of the labeled RNA from the labeled RNA pool having a high binding affinity for the column is retained on the affinity column.

6. The method of claim 1, wherein the affinity column is an ATP-agarose affinity column.

7. The method of claim 1, wherein the reporter molecule comprises one or more fluors or further comprises molecules that modulate the properties of said fluors.

8. The method of claim 7, wherein the fluor is a fluorescent dye wherein a fluorescent dye-nucleotide conjugate is formed.

9. The method of claim 8, wherein the fluorescent dye is selected from the group consisting of fluorescein, Cascade Blue, Texas Red and Rhodamine Green.

10. The method of claim 8, wherein the fluorescent dye-nucleotide conjugate is a fluorescent dye-uridine 5'-triphosphate conjugate.

11. The method of claim 10, wherein the fluorescent uridine 5'-triphospate conjugate is selected from the group consisting of fluorescein-12-UTP, cascade blue-7-UTP, Texas red-5-UTP, and rhodamine green-5-UTP.

12. The method of claim 1, wherein the signaling aptamer is selected from the group consisting of raf15, raf17, raf17-U61C, raf17-U52C, raf17s, raf134, raf110, raf111, raf18, raf133, raf117, raf114, raf120, raf126, raf128, racb7b, and rarg7b.

13. A method of selecting signaling aptamers in vitro comprising the steps of:
   (a) synthesizing a DNA pool, said DNA having a random insert of fifty-one nucleotides, wherein a A:C:G:T mole ratio of amounts of each nucleotide in said random insert is skewed such that the amounts of three of said nucleotides are about equal and substantially comprise a total amount of all nucleotides in said random insert;
   (b) amplifying the DNA pool wherein a nucleotide used in the DNA amplification is labeled with one or more reporter molecules;
   (c) isolating the labeled single-stranded DNA from the amplified DNA;
   (d) applying the labeled single-stranded DNA pool to an affinity column wherein labeled single-stranded DNA molecules having a high binding affinity for the column are retained on the affinity column and thereby removed from the labeled DNA pool;
   (e) repeating steps (a) through (d) to retain the labeled single-stranded DNAs from the labeled DNA pool having a high binding affinity for the column on the affinity column; and
   (f) cloning the retained labeled DNA molecules, said clones comprising signaling aptamers.

14. The method of claim 13, wherein the nucleotide used in the DNA amplification is a modified nucleotide.

15. The method of claim 13, wherein the DNA having the random insert of fifty-one nucleotides has the sequence shown in SEQ ID NO: 1.

16. The method of claim 13, wherein the skewed mole ratio of the random insert of said nucleotides is 3:3:2:0.38 A:C:G:T.

17. The method of claim 13, wherein the affinity column is an ATP-agarose affinity column.

18. The method of claim 13, wherein the reporter molecule comprises one or more fluors or further comprises molecules that modulate the properties of said fluors.

19. The method of claim 18, wherein the fluor is a fluorescent dye such that a fluorescent dye-nucleotide conjugate is formed.

20. The method of claim 19, wherein the fluorescent dye is selected from the group consisting of fluorescein, Cascade Blue, Texas Red and Rhodamine Green.

* * * * *

SEQUENCE LISTING

```
<160> NUMBER OF SEQ ID NOS: 19

<210> SEQ ID NO 1
<211> LENGTH: 102
<212> TYPE: DNA
<213> ORGANISM: artificial sequence
<220> FEATURE:
<221> NAME/KEY: primer_bind
<222> LOCATION: 31..81
<223> OTHER INFORMATION: Sequence of 102-mer oligonucleotide used to
      synthesize RNA signaling aptamer; n = any
      and is a random insert of 3:3:2:0.38 A:C:G:T

<400> SEQUENCE: 1
taatacgact cactataggg aaggcacgac nnnnnnnnnn nnnnnnnnnn          50
nnnnnnnnnn nnnnnnnnnn nnnnnnnnnn nagacccaac cagccagaga         100
cc                                                             102

<210> SEQ ID NO 2
<211> LENGTH: 85
<212> TYPE: RNA
<213> ORGANISM: artificial sequence
<220> FEATURE:
```

```
<221> NAME/KEY: misc_RNA
<222> LOCATION: 14..64
<223> OTHER INFORMATION: Sequence of the RNA pool used for selection.
      n = any and is a random insert of 33.1% A, C, and
      G, 6% U.  Uridine residues are replaced by F-12-U.

<400> SEQUENCE: 2
gggaaggcac gacnnnnnnn nnnnnnnnnn nnnnnnnnnn nnnnnnnnnn          50
nnnnnnnnnn nnnnagaccc aaccagccag agacc                          85

<210> SEQ ID NO 3
<211> LENGTH: 40
<212> TYPE: RNA
<213> ORGANISM: artificial sequence
<220> FEATURE:
<223> OTHER INFORMATION: Minimal anti-adenosine aptamer ATP-40-1
<300> PUBLICATION INFORMATION:
<301> AUTHORS: Sassanfar, M.
      Szostak, J.W.
<302> TITLE: An RNA motif that binds ATP
<303> JOURNAL: Nature
<304> VOLUME: 364
<306> PAGES: 550-553
<307> DATE: 1994

<400> SEQUENCE: 3
ggguugggaa gaaacugugg cacuucggug ccagcaaccc                     40

<210> SEQ ID NO 4
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf15 in Family 1

<400> SEQUENCE: 4
gaagcaagca ggcaacgaac acagaagacc gggggaacua ccgcgcgugc u        51

<210> SEQ ID NO 5
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf17 in Family 1

<400> SEQUENCE: 5
gaagcaagca ggcaacgaac acagaagacc gggggaacua ccgcgcgugc c        51

<210> SEQ ID NO 6
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf134 in Family 1

<400> SEQUENCE: 6
gaagcaagca ggcaacgaac acagaagacc gggggaacua ccgcgcgugc g        51

<210> SEQ ID NO 7
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf110 in Family 2
```

<400> SEQUENCE: 7
cgcggguaaa cagggggcaaa agcggcaggg cccagaagga uaacaguagc a            51

<210> SEQ ID NO 8
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf111 in Family 3

<400> SEQUENCE: 8
aggggacgga gcccuaagac aaaggagggc ggcaggaugc caaacaggua g             51

<210> SEQ ID NO 9
<211> LENGTH: 53
<212> TYPE: RNA
<213> ORGANISM: artificial sequence
<220> FEATURE:
<223> OTHER INFORMATION: Sequence of the 53 nucleotide random region
      from cloned aptamer raf18 in Family 3

<400> SEQUENCE: 9
aggggacgga gccccaaaga caaaggaggg cggcaggaug ccagaacagg uag           53

<210> SEQ ID NO 10
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf133 in Family 3

<400> SEQUENCE: 10
aggggacgga gcccaaagac aaaggagggc ggcaggaagc caaacaggua g             51

<210> SEQ ID NO 11
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf133 in Family 4

<400> SEQUENCE: 11
gaagagccgg cggcgaggcg cgaggccagg aagaaccggc cgcacggagg g             51

<210> SEQ ID NO 12
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf114 in Family 5

<400> SEQUENCE: 12
gcaccgacga ggaggaggag gggagaggaa gggcgccgua gccggcgggg g             51

<210> SEQ ID NO 13
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf120 in Family 5

-continued

<400> SEQUENCE: 13
gcaccgacga ggagguggag gggagaggaa gggcgccgua gccgggaagg g          51

<210> SEQ ID NO 14
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf126 in Family 5

<400> SEQUENCE: 14
gaggccagga gacgaaaggc gaaccaacaa ggcaggcaga gcccggugca c          51

<210> SEQ ID NO 15
<211> LENGTH: 51
<212> TYPE: RNA
<213> ORGANISM: artificial sequence
<220> FEATURE:
<223> OTHER INFORMATION: Sequence of the 51 nucleotide random region
      from cloned aptamer raf128 in Family 5

<400> SEQUENCE: 15
cgcgcaagau accgcccgac agcggaagga ggggcaugcg guccagggcu g          51

<210> SEQ ID NO 16
<211> LENGTH: 6
<212> TYPE: RNA
<213> ORGANISM: artificial sequence
<220> FEATURE:
<223> OTHER INFORMATION: Sequence of the 6 nucleotide motif shared by
      Families 1 and 2

<400> SEQUENCE: 16 cagaag                                                             6

<210> SEQ ID NO 17
<211> LENGTH: 85
<212> TYPE: RNA
<213> ORGANISM: artificial sequence
<220> FEATURE:
<222> LOCATION: 52, 60
<223> OTHER INFORMATION: Sequence of the cloned aptamer raf17 in
      Family 1;u is 12-F-u at positions 52 and 61

<400> SEQUENCE: 17
gggaaggcac gacgaagcaa gcaggcaacg aacacagaag accgggggaa            50
cuaccgcgcg ugccagaccc aaccagccag agacc                            85

<210> SEQ ID NO 18
<211> LENGTH: 85
<212> TYPE: RNA
<213> ORGANISM: artificial sequence
<220> FEATURE:
<222> LOCATION: 52
<223> OTHER INFORMATION: Sequence of the cloned aptamer raf17-U61C in
      Family 1; u is 12-F-u at position 52

<400> SEQUENCE: 18
gggaaggcac gacgaagcaa gcaggcaacg aacacagaag accgggggaa            50
cuaccgcgcg cgccagaccc aaccagccag agacc                            85

<210> SEQ ID NO 19
<211> LENGTH: 61
<212> TYPE: RNA

-continued

```
<213> ORGANISM: artificial sequence
<220> FEATURE:
<222> LOCATION: 48
<223> OTHER INFORMATION: Sequence of the cloned aptamer raf17s in
      Family 1; u is 12-F-u at position 48

<400> SEQUENCE: 19
gggcgcgacg aagcaagcag gcaacgaaca cagaagaccg ggggaacuac          50
cgcgcgcgcc c                                                   61
```